US007946980B2

(12) United States Patent
Reddy et al.

(10) Patent No.: US 7,946,980 B2
(45) Date of Patent: May 24, 2011

(54) MODULAR, ZONE-SPECIFIC MEDICAL ELECTRICAL LEAD DESIGN

(75) Inventors: G. Shantanu Reddy, Minneapolis, MN (US); Matthew S. Finlay, Brooklyn Park, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 281 days.

(21) Appl. No.: 12/371,268

(22) Filed: Feb. 13, 2009

(65) Prior Publication Data

US 2009/0210044 A1 Aug. 20, 2009

Related U.S. Application Data

(60) Provisional application No. 61/028,961, filed on Feb. 15, 2008.

(51) Int. Cl.
*A61B 1/04* (2006.01)
(52) U.S. Cl. ..................... 600/122
(58) Field of Classification Search .............. 29/854; 600/373; 607/115, 122, 127
See application file for complete search history.

(56) References Cited

U.S. PATENT DOCUMENTS

| | | | |
|---|---|---|---|
| 5,231,996 | A | 8/1993 | Bardy et al. |
| 5,246,014 | A | 9/1993 | Williams et al. |
| 5,358,516 | A | 10/1994 | Myers et al. |
| 5,674,272 | A | 10/1997 | Bush et al. |
| 5,845,396 | A | 12/1998 | Altman et al. |
| 5,931,862 | A | 8/1999 | Carson |
| 6,717,056 | B2 | 4/2004 | Rivelli et al. |
| 7,238,883 | B2 | 7/2007 | Zarembo |
| 7,292,894 | B2 | 11/2007 | Belden |
| 7,366,573 | B2 | 4/2008 | Knapp et al. |
| 7,519,432 | B2 | 4/2009 | Bolea et al. |
| 2009/0319012 | A1* | 12/2009 | Garabedian et al. .......... 607/115 |

FOREIGN PATENT DOCUMENTS

| | | |
|---|---|---|
| EP | 1 844 812 A1 | 10/2007 |
| WO | WO 02/087689 | 11/2002 |
| WO | WO 02/089909 | 11/2002 |

OTHER PUBLICATIONS

International Search Report and Written Opinion issued in PCT/US2009/034083, mailed May 11, 2009, 14 pages.
International Search Report and Written Opinion issued in PCT/US2009/034086, mailed May 18, 2009, 13 pages.
Gallik, Donna M. et al., "Lead Fracture in Cephalic Versus Subclavian Approach with Transvenous Implantable Cardioverter Defibrillator Systems" PACE, vol. 19, Jul. 1996, pp. 1089-1094.
Magney, Jean E. et al., "Pacemaker and Defibrillator Lead Entrapment: Case Studies", PACE, vol. 18, Aug. 1995, pp. 1509-1517.
Magney, Jean E. et al., "Anatomical Mechanisms Explaining Damage to Pacemaker Leads, Defibrillator Leads, and Failure of Central Venous Catheters Adjacent to the Sternoclavicular Joint", PACE, vol. 16, Mar. 1993, Part 1, pp. 445-457.

(Continued)

*Primary Examiner* — George Manuel
*Assistant Examiner* — Robert N Wieland
(74) *Attorney, Agent, or Firm* — Faegre & Benson LLP (57) ABSTRACT

A medical electrical lead configured to be coupled to a pulse generator in a cardiac rhythm management system. The lead comprises a proximal terminal connector configured for coupling the lead to the pulse generator, and a plurality of longitudinally arranged lead segments each configured to exhibit one or more predetermined physical characteristics based on the implantation location for the respective segment. The lead segments may be pre-fabricated as separate modules optimized for the operating environment and/or delivery requirements of the respective segments. The pre-fabricated modules are longitudinally arranged and joined to form the lead.

20 Claims, 4 Drawing Sheets

OTHER PUBLICATIONS

Magney, Jean E. et al., "A New Approach to Percutaneous Subclavian Venipuncture to Avoid Lead Fracture or Central Venous Catheter Occlusion", PACE, vol. 16, Nov. 1993, pp. 2133- 2142.

Roelke, Marc et al., "Subclavian Crush Syndrome Complicating Transvenous Cardioverter Defibrillator Systems", PACE, vol. 18, May 1995, Part 1, pp. 973-979.

* cited by examiner

MODULAR, ZONE-SPECIFIC MEDICAL ELECTRICAL LEAD DESIGN

CROSS-REFERENCE TO RELATED APPLICATION

This application claims priority to U.S. Provisional Application No. 61/028,961, filed Feb. 15, 2008, which is incorporated herein by reference in its entirety.

TECHNICAL FIELD

The present invention relates to medical electrical leads for use in cardiac rhythm management systems, and in particular, to medical electrical leads configured for partial implantation in a heart of a patient.

BACKGROUND

Various types of medical electrical leads for use in cardiac rhythm management systems are known. Such leads typically extend intravascularly to an implantation location within or on a patient's heart, and thereafter coupled to a pulse generator or other implantable device for sensing cardiac electrical activity, delivering therapeutic stimuli, and the like. The leads are desirably highly flexible to accommodate natural patient movement, yet also constructed to have minimized profiles. At the same time, the leads are exposed to various external forces imposed, for example, by the human muscular and skeletal system, the pulse generator, other leads, and surgical instruments used during implantation and explantation procedures. There is a continuing need for improved lead designs.

SUMMARY

The present invention, in one embodiment, is a method of making an implantable medical electrical lead. The method comprises providing a plurality of pre-fabricated lead modules each corresponding to a lead segment configured for a predetermined implantation site, including providing a first module defining to a first proximal lead segment, providing a second module defining to a second proximal lead segment, providing a third module defining to an electrode lead segment, and providing a fourth module defining to a distal fixation segment including a fixation helix. The method further comprises longitudinally assembling and joining the first, second, third and fourth modules.

In another embodiment, the present invention is a method of making an implantable medical electrical lead adapted to be at least partially implanted in a heart of a patient and to be coupled to a pulse generator of a cardiac rhythm management system. The method comprises configuring each of a plurality of pre-fabricated lead segments to exhibit one or more desired physical characteristics depending on an implantation location of the respective segment. The lead segments include at least one segment configured for subcutaneous implantation and to exhibit one or more of a greater stiffness, crush resistance, cut resistance, or temperature resistance than each of the other of the plurality of segments. The lead segments further include at least one segment configured for intravascular implantation and to exhibit one or more of a greater flexibility and smaller outside diameter than the at least one segment configured for subcutaneous implantation, and at least one segment configured for intracardiac implantation and to exhibit one or more of a greater flexibility and smaller outside diameter than the at least one segment configured for subcutaneous implantation. The method further includes longitudinally arranging and coupling the lead segments.

In yet another embodiment, the present invention is a medical electrical lead configured to be coupled to a pulse generator in a cardiac rhythm management system. The lead comprises a proximal terminal connector configured for coupling the lead to the pulse generator, and a plurality of longitudinally arranged pre-fabricated lead segments. The pre-fabricated lead segments include a first proximal segment coupled the terminal connector, a second proximal segment coupled to and extending distally from the first proximal segment, an electrode segment coupled to and extending distally from the second proximal segment and including an electrode configured to be electrically coupled to the pulse generator to deliver an electrical stimulus to a patient, and a distal fixation segment coupled to and extending distally from the distal electrode segment and configured to secure the lead to the cardiac tissue. Each segment is coupled to an adjacent segment by a joint.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
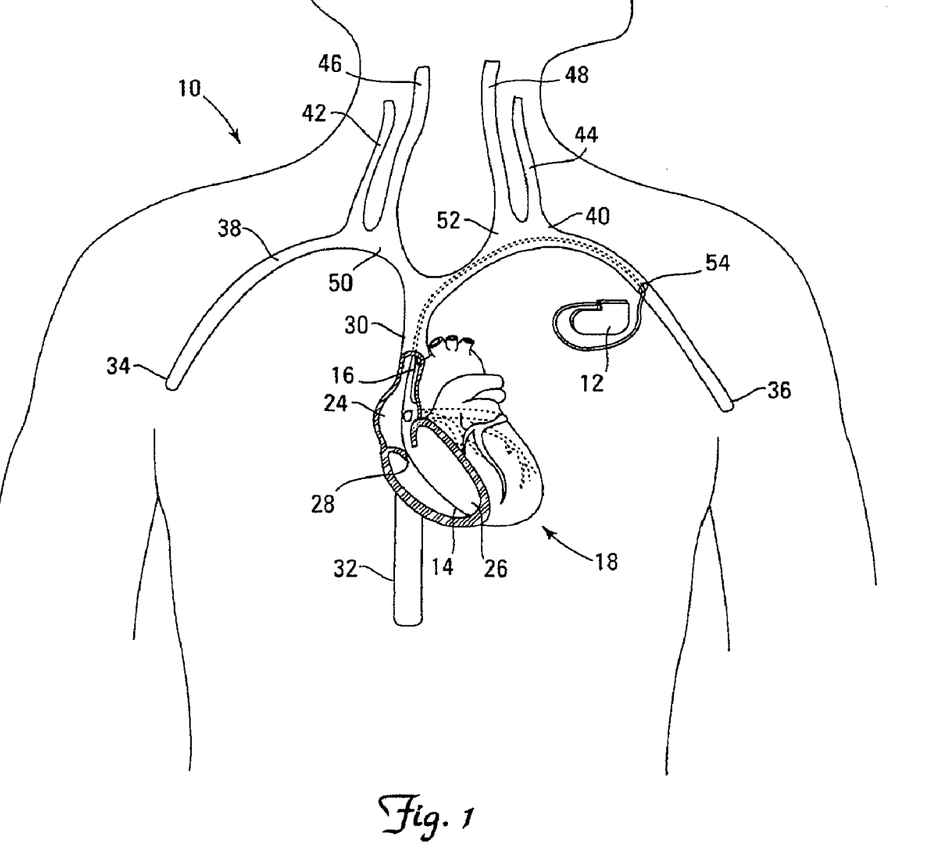
FIG. 1 is a schematic view of a cardiac rhythm management (CRM) system including a pulse generator and a plurality of leads according to an embodiment of the present invention.

FIG. 1 is a schematic view of a cardiac rhythm management (CRM) system 10 according to an embodiment of the present invention. As shown in FIG. 1, the CRM system 10 includes a pulse generator 12 coupled to a plurality of leads 14, 16 deployed in a patient's heart 18. As further shown in FIG. 1, the heart 18 includes a right atrium 24 and a right ventricle 26 separated by a tricuspid valve 28. During normal operation of the heart 18, deoxygenated blood is fed into the right atrium 24 through the superior vena cava 30 and the inferior vena cava 32. The major veins supplying blood to the superior vena cava 30 include the right and left axillary veins 34 and 36, which flow into the right and left subclavian veins 38 and 40. The right and left external jugular 42 and 44, along with the right and left internal jugular 46 and 48, join the right and left subclavian veins 38 and 40 to form the right and left brachiocephalic veins 50 and 52, which in turn combine to flow into the superior vena cava 30.

The leads 14, 16 operate to convey electrical signals and stimuli between the heart 18 and the pulse generator 12. In the illustrated embodiment, the lead 14 is implanted in the right ventricle 26, and the lead 16 is implanted in the right atrium 24. In other embodiments, the CRM system 10 may include additional leads, e.g., a lead extending into a coronary vein for stimulating the left ventricle in a bi-ventricular pacing or cardiac resynchronization therapy system. As shown, the leads 14, 16 enter the vascular system through a vascular entry site 54 formed wall of the left subclavian vein 40, extend through the left brachiocephalic vein 52 and the superior vena cava 30, and are implanted in the right ventricle 26 and right atrium 24, respectively. In other embodiments, the leads 14, 16 may enter the vascular system through the right subclavian vein, the left axillary vein 36, the left external jugular 44, the left internal jugular 48, the left brachiocephalic vein 52, or other suitable vascular access locations.

The pulse generator 12 is typically implanted subcutaneously within an implantation location or pocket in the patient's chest or abdomen. The pulse generator 12 may be any implantable medical device known in the art or later developed for delivering an electrical therapeutic stimulus to the patient. In various embodiments, the pulse generator 12 is a pacemaker, an implantable cardiac defibrillator, and/or includes both pacing and defibrillation capabilities. The portions of the leads 14, 16 extending from the pulse generator 12 to the vascular entry site 54 are also located subcutaneously or submuscularly. Any excess lead length, i.e., length beyond that needed to reach from the pulse generator 12 location to the desired intracardiac implantation site, is generally coiled up in the subcutaneous pocket near the pulse generator 12.

Figure 2A:
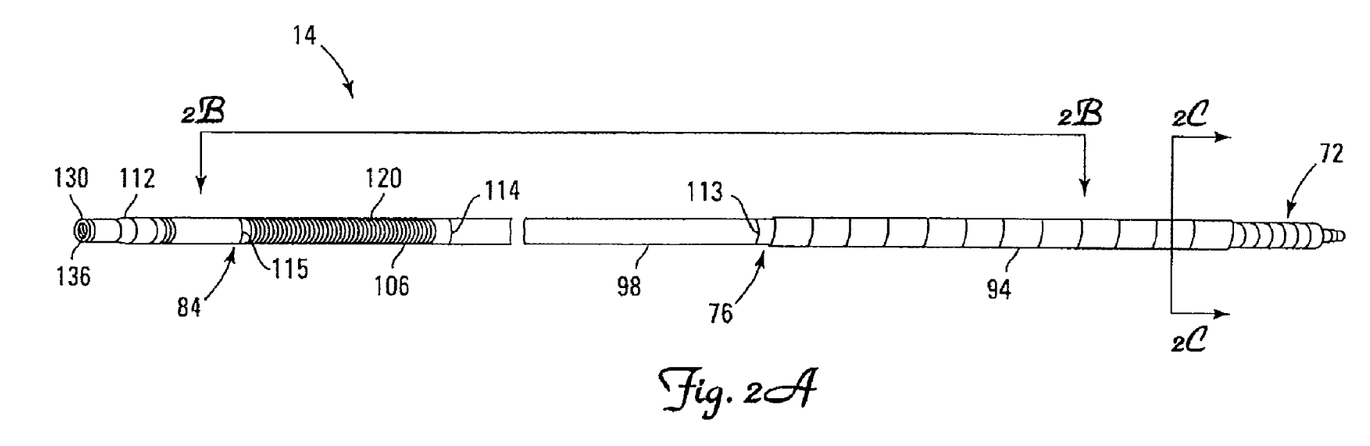
FIG. 2A is an isometric illustration of one of the leads of FIG. 1 according to one embodiment of the present invention.

FIG. 2A is an isometric illustration of the lead 14 according to one embodiment of the present invention. As shown in FIG. 2A, the lead 14 includes, in one embodiment, a connector 70, a proximal portion 76, and a distal portion 84. As further shown, the proximal portion 76 is coupled to and extends distally from the connector 70, and the distal portion 84 is coupled to and extends distally from the proximal portion 76. The connector 70 is configured to mechanically and electrically couple the lead 14 to a header on the pulse generator 12. In various embodiments, the proximal portion 76 is dimensioned to extend from the implanted pulse generator 12 and into the vascular system. Thus, part of the proximal portion 76 is located generally subcutaneously when the lead 14 is implanted, with the remaining part extending intravascularly, i.e., from just distal to the vascular entry site 54, through the left subclavian vein 40 and the left brachiocephalic vein 52. The distal portion 84 is dimensioned to extend from the proximal portion 76, through the superior vena cava 30 and right atrium 24 to a location in the right ventricle 26.

As shown, the proximal and distal portions 76, 84 are each formed from a plurality of longitudinally-arranged lead segments. Thus, in the illustrated embodiment, the proximal portion 76 includes a first proximal segment 94 and a second proximal segment 98 coupled to and extending distally from the first proximal segment 94. Additionally, the distal portion 84 includes an electrode segment 106 and a distal fixation segment 112. As further shown, the respective adjacent segments are coupled together at joints 113, 114, and 115.

In the illustrated embodiment, the electrode segment 106 includes a flexible coil electrode 120 operable as a shocking electrode for providing a defibrillation shock to the heart 18. The coil electrode 120 can be of any configuration suitable for implantable defibrillation leads, whether now known or later developed. In one embodiment, the coil electrode 120 includes a coating configured to control (i.e., promote or discourage) tissue in-growth. In one embodiment, the electrode 120 is coated with an expanded polytetrafluoroethylene (ePTFE) coating configured to permit intimate fluid contact between the electrode 120 and the cardiac tissue and also to substantially prevent tissue ingrowth and fibrosis that could otherwise adhere to the electrode surfaces. In one embodiment, the coil electrode 120 is uncoated.

As further shown, the distal fixation segment 112 includes a distal tip 130 from which an extendable/retractable fixation helix 136 can be extended to penetrate the cardiac tissue to secure the distal tip 130 of the lead 14 thereto. In such embodiments, the fixation helix 136 is mechanically coupled to a mechanism, e.g., a rotatable terminal pin of the terminal connector 70 operable by the implanting physician to extend and retract the helix 136 as necessary. In other embodiments, the fixation helix 136 is a fixed helix (i.e., not extendable/retractable) and may be covered by a dissolvable material to prevent the helix 136 from catching on body tissue during delivery to the implantation site. In still other embodiments, other fixation means, e.g., tines, pre-formed and pre-biased lead portions, stents, etc. are employed. In various embodiments, the fixation helix 136 is also configured as a pace/sense electrode, and thus is electrically coupled to the pulse generator 12 via the connector 70 (see FIG. 1). In various other embodiments, other electrode configurations may be employed depending on the particular therapeutic needs of the patient.

Figure 2B:
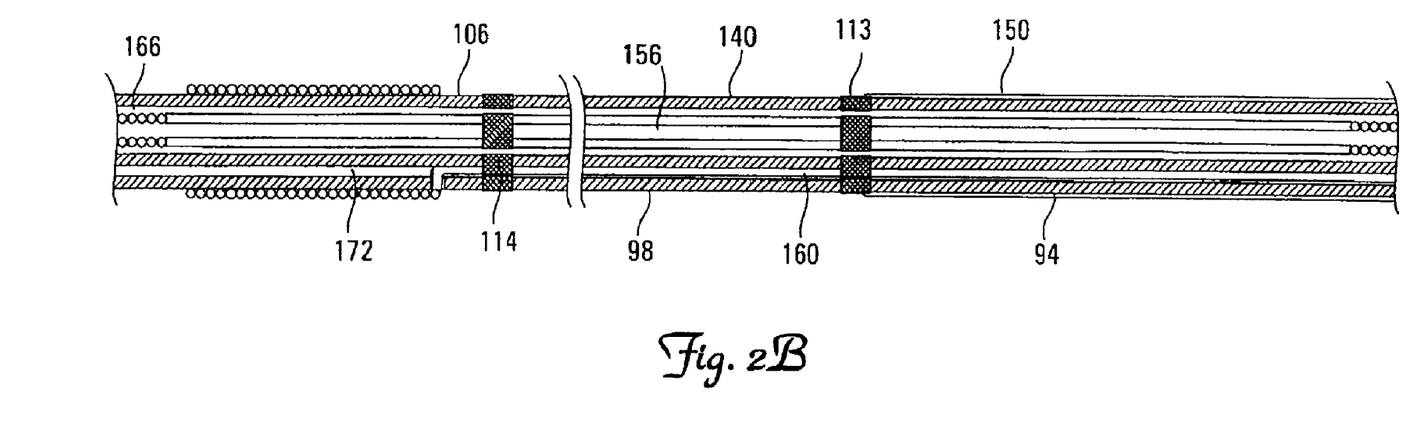
FIGS. 2B and 2C are enlarged longitudinal and transverse cross-sectional views of a portion the lead of FIG. 2A taken along the lines 2B-2B and 2C-2C, respectively, in FIG. 2A.
Figure 2C:
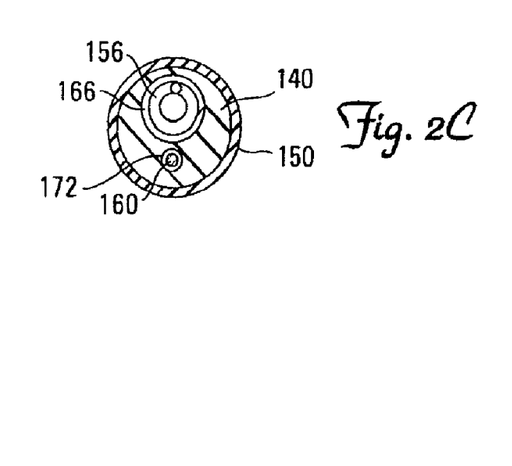

FIGS. 2B and 2C are longitudinal and transverse cross-sectional views of a portion of the lead 14 taken along the lines 2B-2B and 2C-2C, respectively, in FIG. 2A. As shown, the lead 14 includes a main body member 140, a reinforcing layer 150, a coil conductor 156, and a cable conductor 160. As shown, the body member 140 includes a pair of longitudinal lumens 166, 172 in which the coil and cable conductors 156, 160 reside.

In various embodiments, the coil conductor 156 is mechanically and electrically coupled to the fixation helix 136 and to the terminal connector 70. Thus, as will be appreciated, the coil conductor 156 operates to convey electrical signals between the fixation helix 136 and the connector 70, and thus also to the pulse generator 12. The coil conductor 156 also operates to transmit torque applied at the connector 70 (e.g., via a rotatable terminal pin) to the fixation helix 136 for extending and retracting the fixation helix 136 as required. The cable conductor 160 is mechanically and electrically coupled to the coil electrode 120, and thus operates to convey electrical signals between the coil electrode 120 and the connector 70 and pulse generator 12.

As shown, the lead body member 140 extends longitudinally from the connector 70 to the distal fixation segment 112, and through the coil electrode 120. As further shown, in the illustrated embodiment, the lead body member 140 is circumferentially covered by the reinforcing layer 150 in the first proximal segment 94.

Any conventional or later developed materials suitable for medical electrical lead construction can be used to construct the lead 14. For example, the lead body member 140 can be made from any flexible, biocompatible materials suitable for lead construction. In various embodiments, the lead body member 140 is made from a flexible, electrically insulative material such as silicone rubber. Similarly, the connector 70, the coil and cable conductors 156, 160, the coil electrode 120, the fixation helix 136, and the corresponding extension/retraction mechanism (not shown), if present, may be made from any conventional or later developed materials suitable for such uses.

In the various embodiments of the present invention, the respective lead segments are each configured for implantation in a different region of the patient's body, and accordingly, are configured to exhibit specific physical and functional characteristics depending on the respective implantation locations. In one embodiment, the first proximal segment is configured to be implanted substantially subcutaneously, i.e., in the "pocket" region in which the pulse generator 12 is also implanted, while the second proximal segment 98 is configured to be implanted primarily intravascularly, e.g., within the left subclavian vein 40 and the left brachiocephalic vein 52 and into the superior vena cava 30 (see FIG. 1). Additionally, the electrode segment 106 and the fixation segment 112 are configured to be implanted within the right atrium 26 and/or right ventricle 24, and are thus configured for intracardiac implantation.

Because the various lead segments described above are configured to occupy different implantation locations, the respective segments are likely to be subject to different operating and delivery conditions. According to various embodiments of the present invention, the various segments are therefore configured differently to optimize the performance of the lead in light of these differing operating environments and delivery conditions. Additionally, in various embodiments, the respective lead segments are pre-fabricated as separate modules and assembled to form the lead 14.

For example, the subcutaneously implanted first proximal segment 94 may, in various circumstances, be subject to abrasion and crushing loads imparted by interaction of the lead 14 with other leads, the pulse generator 12, and/or the skeletal and muscular systems of the patient itself. Additionally, suture sleeves may be disposed about the lead 14 in the subcutaneous first proximal segment 94 to secure the lead 14 to the adjacent fascial tissue. As will be appreciated, use of sutures to secure the lead 14 to the tissue imparts a compressive force on the lead 14.

The subcutaneous first proximal segment 94 may also be subjected to damage (e.g., cutting, burning, etc.) by various surgical instruments. For example, an electrocautery instrument or mechanical cutting instrument (e.g., a scalpel) may be used to cut fibrosed tissue away from the bodies of implanted leads to allow such leads to be removed and/or replaced as necessary. In such circumstances, the electrocautery instrument or scalpel may inadvertently damage the insulative covering of an adjacent lead that is not otherwise intended to be removed. In this regard, in some embodiments, it may be desirable to configure the first proximal segment 94 to resist fibrotic tissue encapsulation in the first instance.

Additionally, in some circumstances, the proximal portion 76 of the lead may advantageously be made relatively stiff compared to the distal portion 84 so as to enhance the pushability and/or torqueability of the lead 14 during delivery.

At the same time, however, the intravascularly implanted second proximal segment 98 may, in various applications, not be subjected to external forces and loads comparable to those imposed on the subcutaneous first proximal segment 94. In contrast, the second proximal segment 98 is advantageously made highly flexible to accommodate natural cardiac motion, and is also configured to have a minimum profile in light of the relatively confined spaces in which it is implanted. Similarly, different operating and use considerations apply to the electrode and distal fixation segments 106, 112 as compared to the subcutaneously implanted first proximal segment 94.

Accordingly, in various embodiments of the present invention, the lead segments are each specifically designed and optimized based on their respective operating environments and/or desired functionality. For example, in various embodiments, the subcutaneously implanted first proximal segment 94 is optimized to have enhanced fatigue properties and for enhanced resistance to damage from cutting, high temperatures (e.g., electrocautery), crushing, and/or fibrotic encapsulation.

In the illustrated embodiment, the first proximal segment 94 includes the reinforcing layer 150 to enhance the abrasion, crush, temperature, and/or cut resistance as well as stiffness of this portion of the lead. In one embodiment, the reinforcing layer 150 is also configured to substantially prevent tissue ingrowth and fibrotic tissue encapsulation.

In some embodiments, the reinforcing layer 150 is configured as an armoring layer such as is described in co-pending and commonly assigned U.S. Provisional Patent Application No. 61/028,999 to Reddy filed on Feb. 15, 2008 and titled "Medical Electrical Lead with Proximal Armoring" and U.S. patent application Ser. No. 12/371,264, to Reddy filed on same date as the present application and titled "Medical Electrical Lead with Proximal Armoring," both of which is incorporated herein by reference in their entirety. In one embodiment, the reinforcing layer 150 includes a lubricious, flexible ribbon of polymeric material, e.g., polytetrafluoroethylene (PTFE) or expanded polytetrafluoroethylene (ePTFE) disposed over the lead body 70.

In various other embodiments, the lead body member 140 in the first proximal segment 94 includes a reinforcing braid, wire, mesh, or other functionally comparable structure in lieu of or in addition to the reinforcing layer 150 to enhance the desired physical characteristics of the first proximal segment 94. In other embodiments, however, the lead optimization is accomplished by material selection, e.g., by making the lead body member 140 out of a highly lubricious and/or relatively stiff polymer, materials that are resistant to electrocautery damage (e.g., ePTFE), and the like.

The remaining segments of the lead 14 are also specifically tailored and optimized for their own operating environments. In various embodiments, the intravascularly implanted second proximal segment 98 is configured to provide one or more of a minimized profile (e.g., outer diameter), high flexibility, and/or resistance to tissue adhesion and attachment to the venous walls.

Similarly, in various embodiments, the electrode segment 106 is optimized for enhanced electrical performance, reduced size, fatigue resistance, high flexibility, and to prevent tissue ingrowth. In various embodiments, the electrode segment 106 includes a pre-formed bias so as to tend to urge the electrode 120 into the cardiac tissue when implanted. Optimization of the distal fixation segment 112 includes, without limitation, configuring this segment to promote tissue ingrowth for enhanced fixation and stability, enhanced electrical performance (i.e., when the fixation helix 136 is also operative as a pace/sense electrode), and/or to be substantially atraumatic. In some embodiments, the distal fixation segment 112 is also pre-curved, e.g., in a J-shape, to urge the fixation helix 136 to a desired position in the heart 18. Of course, the foregoing examples are illustrative only, and in no way limiting.

The means for optimizing the respective lead segments are not limited, and can be accomplished by the inclusion or omission of additional structure (e.g., the reinforcing layer 150), by selecting materials having the desired properties, varying dimensions of the various segments, and the like. In various embodiments, for example, the optimization features are incorporated into the lead body member 140, the coil and/or cable conductors 156, 160, the electrode 120, or any of the above. Again, the various embodiments of the present invention encompass any suitable means for optimization of the respective lead body segments for their specific service conditions.

As discussed above, the first and second proximal lead segments 94, 98, the electrode segment 106, and the distal fixation segment 112 are advantageously pre-fabricated as separate modules and subsequently assembled and joined to form the completed lead 14. For example, in on embodiment, the proximal fixation segment 94 includes, in predetermined lengths, a section of the lead body member 140, the outer tubing 146, the reinforcing layer 150, and the coil and cable conductors 156, 160. Similarly, the second proximal segment 98 includes a section of the lead body member 140, and the coil and cable conductors 156, 160. The electrode segment 106 can in turn be pre-assembled to include an additional section of the lead body member 140, the coil and cable conductor 156, 160, and the coil electrode 120. Finally, the distal fixation segment 112 is pre-fabricated to include the fixation helix/electrode 136 and the associated internal mechanisms for facilitating extension and retraction of the helix 136.

To form the lead 14, the respective pre-fabricated modules are assembled and joined longitudinally. For example, the conductor sections for adjacent segments are electrically and mechanically connected via a suitable joining process, e.g., crimping, welding, and the like. In various embodiments, crimp tubes or comparable structures known in the art are included on the modules to facilitate coupling the conductor sections in the adjacent lead segments. Similarly, the sections of the lead body member 140 in adjacent lead segments are joined via a suitable process for joining polymeric materials, e.g., using medical adhesive, shrink tubing, and the like. Additionally, the sections of the lead body member 140 in the respective lead segments may include windows through their outer surfaces near the ends of the segments, or similar features to provide access for facilitating coupling the conductor sections of the adjacent segments.

In various embodiments, one or more of the pre-fabricated lead modules may not include any or all of the conductor sections, thus avoiding multiple conductor joints along the length of the lead 14. For example, in one embodiment, the first and second proximal lead segments 94, 98, the electrode segment 106, and the distal fixation segment 112 do not include sections of the coil and cable conductors 156, 160, so that these conductors can be provided in uninterrupted lengths. Thus, the lead 14 could be assembled by coupling the conductors 156, 160 to respective electrical contacts on the connector 70, and then sliding the first and second proximal lead segments 94, 98, the electrode segment 106, and the distal fixation segment 112 over the conductors 156, 160. The required mechanical and electrical connections are made between the coil conductor 156 and the fixation helix 136, and also between the cable conductor 160 and the coil electrode 120, using any suitable joining technique, e.g., crimping, welding, and the like. The polymeric lead body sections are then spliced and joined using a suitable polymer joining technique, e.g., medical adhesive, shrink-tubing, and the like.

The pre-fabricated modular construction of the segmented lead 14 has numerous advantages. For example, the respective lead segment modules can be mass produced in various lengths, diameters, and/or to conform to other specific specifications (e.g., crush or abrasion resistance, high temperature compatibility for electrocautery damage resistance, flexibility, and the like). These modules can then be combined to create wide ranges of lead configurations. Assembly of the pre-fabricated modules also advantageously provides manufacturing efficiencies in some circumstances. For example, providing one or more modules with conductor (coil and/or cable) segments which are subsequently joined to the conductors of adjacent modules can eliminate the need to string elongated conductors through the entire length of the lead as is the case in conventional lead designs. Other advantages of the modular, segmented leads of the various embodiments of the present invention will become apparent based on the foregoing.

Figure 3A:
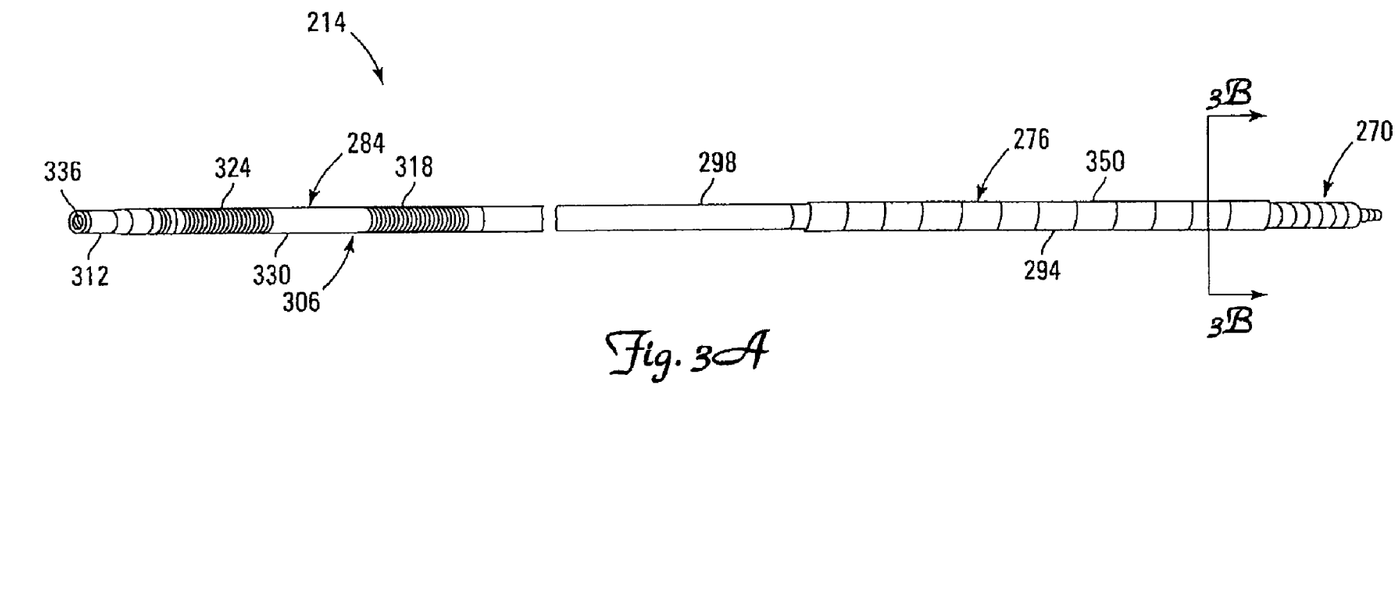
FIG. 3A is an isometric illustration of an alternative lead for use with the CRM system of FIG. 1 according to one embodiment of the present invention.
Figure 3B:
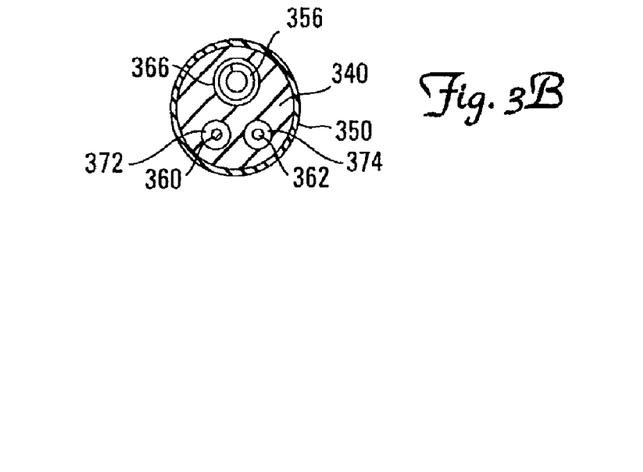
FIG. 3B is an enlarged transverse cross-sectional view of a portion the lead of FIG. 3A taken along the lines 3B-3B.

Although the embodiments illustrated above include a single coil defibrillation electrode 120, other embodiments have different configurations. FIG. 3A is an isometric illustration of an alternative lead 214 for use with the CRM system of FIG. 1, and FIG. 3B is a transverse cross-sectional view of a portion of the lead 214 taken along the line 3B-3B in FIG. 3A, according to an embodiment of the present invention. As shown, the lead 214 includes a connector 270, a proximal portion 276, and a distal portion 284. As further shown, the proximal portion 276 is coupled to and extends distally from the connector 270, and the distal portion 284 is coupled to and extends distally from the proximal portion 276. The connector 270 is configured to mechanically and electrically couple the lead 214 to a header on the pulse generator 12.

Like the corresponding elements of the lead 14 described above, the proximal portion 276 is dimensioned to extend from the implanted pulse generator 12 and into the vascular system, e.g., into the left subclavian vein 40 (see FIG. 1), to the superior vena cava 30. Similarly, the distal portion 284 is dimensioned to extend from the proximal portion 276, through the superior vena cava 30 and right atrium 24 to a location in the right ventricle 26.

As with the lead 14 above, the proximal and distal portions 276, 284 are each formed of a plurality of longitudinally-arranged lead segments. Thus, in the illustrated embodiment, the proximal portion 276 includes a first proximal segment 294 and a second proximal segment 298 coupled to and extending distally from the first proximal segment 294. Additionally, as further shown, the distal portion 284 includes an electrode segment 306 and a distal fixation segment 312.

In the illustrated embodiment, the electrode segment 306 includes a proximal coil electrode 318, a distal coil electrode 324, and a spacer portion 330 therebetween. The proximal coil electrode 318 is coupled to and extends distally from the second proximal segment 298, and the distal fixation segment 312 is coupled to and extends distally from the distal coil electrode 324. Thus, the lead 214 operates as a multi-polar defibrillation lead. As further shown, the distal fixation segment 312 includes a fixation helix 336.

As shown in the cross-sectional view of FIG. 3B, the lead 214 includes a main body member 340, a reinforcing layer 350, a coil conductor 356, and a pair of cable conductors 360, 362. As shown, the body member 340 includes a coil conductor lumen 366 in which the coil conductor 356 resides, and further includes a pair of cable conductor lumens 372, 374 in which the cable conductors 360, 362 reside.

In various embodiments, the coil conductor 356 is mechanically and electrically coupled to the fixation helix 336 and to the terminal connector 270, and operates in much the same or identical manner as the coil conductor 150 of the lead 14. Similarly, each of the cable conductors 360, 362 is mechanically and electrically coupled to one of the coil electrodes 318, 324, and thus operates to convey electrical signals between the respective coil electrode and the connector 270 and pulse generator 12. With the exception of the additional cable conductor and corresponding lumen in the lead 214, the first and second proximal segments 294, 298 and the distal fixation segment 312 operate and are configured, in various embodiments, in substantially the same or an identical manner as the corresponding elements of the lead 14 described above, and thus are not describe in further detail here.

The segments of the lead 214 are also specifically designed and configured so as to provide optimal performance for their respective operating environments and/or delivery conditions. Thus, in various embodiments, the first and second proximal segments 294, 298, the electrode segment 306, and the distal fixation segment 312 are configured in much the same or an identical manner as the corresponding segments of the lead 14. Additionally, the spacer portion 330 of the electrode segment 306 is configured, in various embodiments, for optimal size (typically being relatively small in diameter), high flexibility, and fatigue performance due to the natural movement of the patient's heart.

As with the lead 14, the respective segments of the lead 214 are, in various embodiments, pre-fabricated as separate modules and subsequently assembled and joined to form the completed lead 214. In one embodiment, the electrode segment 306 is a single module including the proximal and distal electrodes 318, 324 and the spacer portion 330, as well as corresponding sections of the main body member 340, the outer tubing 346, the coil conductor 356, and the cable conductors 360, 362. In one embodiment, each of the coil electrodes 318, 324 and the spacer portion 330 are pre-fabricated as a separate module (including corresponding body, outer tubing, and conductor sections). In one embodiment, the spacer portion 330 is pre-fabricated along with one of the electrodes 318 or 324 as a single module. In any case, the respective modules are subsequently assembled and joined in the manner described above with respect to the lead 14.

Although the leads 14, 214 described above are both defibrillation leads including coil shocking electrodes adapted for intracardiac implantation, it will be appreciated that the zone-specific, modular lead construction concepts described herein can also be utilized for any implantable lead configurations, whether now known or later developed. For example, in other defibrillation lead embodiments, the shocking electrodes can take on any other suitable form, e.g., conductive braids, meshes, rings, conductive polymers, and the like. Additionally, various other embodiments of the present invention include right atrial and/or right ventricular pace/sense leads, epicardial pacing and/or defibrillation leads, coronary venous leads configured to be implanted in the coronary veins for left ventricular stimulation, and the like. As will be appreciated, the coil defibrillation electrodes, e.g., the electrode 120, are omitted from such leads. Rather, such leads may include smaller ring or similar electrodes on the lead bodies, tip electrodes, and/or pad electrodes, as are known in the art. In various embodiments, the foregoing pacing leads can be unipolar, or multipolar and can include any suitable conductor configuration, e.g., single or multi-filar coil conductors (coaxial or co-radial design), cable conductors, conductive ribbons, solid wires, and the like. In one embodiment, for example, the lead is a unipolar pacing lead configured for either right atrial, right ventricular, or coronary venous implantation, and includes only a single tip electrode or ring electrode near its distal end.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of making an implantable medical electrical lead, the method comprising:
   providing a plurality of pre-fabricated lead modules each corresponding to a lead segment configured for a predetermined implantation site, including:
      providing a first module defining to a first proximal lead segment;
      providing a second module defining to a second proximal lead segment;
      providing a third module defining to an electrode lead segment; and
   providing a fourth module defining to a distal fixation segment including a fixation helix; and
   longitudinally assembling and joining the first, second, third and fourth modules.

2. The method of claim 1 wherein assembling and joining the lead modules includes joining the first module to the second module, the second module to the third module, and the third module to the fourth module.

3. The method of claim 1 wherein the first proximal lead segment is configured to be implanted subcutaneously, the second proximal segment is configured to be implanted intravascularly, and the electrode and distal fixation segments are configured to be implanted in a cardiac chamber.

4. The method of claim 3 wherein providing the plurality of lead modules includes configuring each of the modules to exhibit one or more physical characteristics depending on the implantation location of the corresponding segment.

5. The method of claim 4 wherein configuring each of the modules includes:
   configuring the first module to exhibit one or more of an enhanced cut resistance, an enhanced crush resistance, an enhanced high temperature resistance, or an enhanced resistance to fibrotic encapsulation, relative to the second, third, or fourth modules.

6. The method of claim 5 wherein configuring each of the modules includes:
   configuring the second and the third modules to have a smaller outside diameter and a greater flexibility than the first module.

7. The method of claim 6 wherein configuring each of the modules includes configuring the fourth module to promote tissue ingrowth.

8. The method of claim 7 wherein:
   providing the first and second modules includes:
      providing first and second lead modules each including a lead body member segment having a first and second longitudinal lumen therethrough;
      a first conductor section extending at least partially within the first lumen; and
      a second conductor extending at least partially within the second lumen; and
   assembling and joining the modules includes:
      joining the first conductor section of the first module to the first conductor section of the second module;
      joining the second conductor section of the first module to the second conductor section of the second module; and
      joining the lead body member sections of the first and second modules.

9. The method of claim 1 wherein providing the third module includes providing a third module including a proximal electrode, a distal electrode, and a spacer portion therebetween.

10. The method of claim 9 wherein the fixation helix is configured to deliver a pacing stimulus to the heart.

11. The method of claim 1 wherein providing the plurality of pre-fabricated lead modules includes providing a plurality of lead modules each configured to exhibit one or more pre-determined physical characteristics depending on the implantation location of the corresponding segment.

12. The method of claim 11 wherein providing the plurality of lead modules includes:
 providing a first module configured to exhibit one or more of an enhanced cut resistance, an enhanced crush resistance, an enhanced high temperature resistance, or an enhanced resistance to fibrotic encapsulation, relative to the second, third, or fourth modules; and
 providing a second, third, and fourth module each configured to exhibit a greater flexibility and a smaller outside diameter than the first module.

13. A method of making an implantable medical electrical lead adapted to be at least partially implanted in a heart of a patient and to be coupled to a pulse generator of a cardiac rhythm management system, the method comprising:
 configuring each of a plurality of pre-fabricated lead segments to exhibit one or more desired physical characteristics depending on an implantation location of the respective segment, the lead segments including:
  at least one segment configured for subcutaneous implantation and to exhibit one or more of a greater stiffness, crush resistance, cut resistance, or temperature resistance than each of the other of the plurality of segments;
  at least one segment configured for intravascular implantation and to exhibit one or more of a greater flexibility and smaller outside diameter than the at least one segment configured for subcutaneous implantation; and
  at least one segment configured for intracardiac implantation and to exhibit one or more of a greater flexibility and smaller outside diameter than the at least one segment configured for subcutaneous implantation; and
 longitudinally arranging and coupling the lead segments.

14. The method of claim 13 wherein the at least one segment configured for intracardiac implantation includes:
 an electrode segment including at least a first electrode configured to deliver an electrical stimulus to the heart; and
 a distal fixation segment including a fixation helix configured to penetrate tissue of the heart to secure the lead thereto and further configured as a second electrode configured to deliver an electrical stimulus to the heart.

15. The method of claim 13 wherein the at least one segment configured for intracardiac implantation includes an electrode located at or near a distal tip of the lead, the electrode configured to deliver a pacing stimulus to the heart.

16. The method of claim 13 wherein the at least one segment configured for subcutaneous implantation includes a reinforcing structure.

17. A medical electrical lead configured to be coupled to a pulse generator in a cardiac rhythm management system, the lead comprising:
 a proximal terminal connector configured for coupling the lead to the pulse generator; and
 a plurality of longitudinally arranged pre-fabricated lead segments including:
  a first proximal segment coupled the terminal connector;
  a second proximal segment coupled to and extending distally from the first proximal segment;
  an electrode segment coupled to and extending distally from the second proximal segment and including an electrode configured to be electrically coupled to the pulse generator to deliver an electrical stimulus to a patient; and
  a distal fixation segment coupled to and extending distally from the distal electrode segment and configured to secure the lead to the cardiac tissue,
 wherein each segment is coupled to an adjacent segment by a joint.

18. The lead of claim 17 wherein the first and second proximal segments each include:
 a flexible, insulative body member section including a lumen extending longitudinally therethrough; and
 an electrical conductor section disposed within the lumen and extending therethrough,
 wherein:
  the conductor sections are mechanically and electrically coupled to each other;
  the conductor section of the first proximal segment is mechanically and electrically coupled to the terminal connector; and
  the conductor section of the second proximal segment is electrically coupled to the electrode.

19. The lead of claim 17 wherein the electrode segment includes a proximal electrode coupled to and extending distally from the second proximal segment, a spacer portion extending distally from the proximal electrode, and a distal electrode extending distally from the spacer portion, wherein the proximal and distal electrodes are configured to be electrically coupled to the pulse generator to deliver an electrical stimulus to the patient.

20. The lead of claim 17 wherein only the first proximal segment includes a reinforcing structure configured to enhance on or more of a stiffness, crush resistance, cut resistance, or temperature resistance of the first proximal segment.

* * * * *